United States Patent [19] [11] 4,352,762
Fahmy [45] Oct. 5, 1982

[54] PROCESS FOR THE PRODUCTION OF S-TERTIARYALKYL PHOSPHONODITHOIC HALIDES

[75] Inventor: Mohamed A. Fahmy, Edison, N.J.
[73] Assignee: Rhone-Poulenc Agrochimie, Lyon, France
[21] Appl. No.: 201,937
[22] Filed: Oct. 29, 1980

Related U.S. Application Data

[63] Continuation of Ser. No. 71,465, Aug. 31, 1979, abandoned.

[51] Int. Cl.³ ................................................ C07F 9/20
[52] U.S. Cl. ................................... 260/972; 260/960; 260/973
[58] Field of Search ............................. 260/973, 972

[56] References Cited
U.S. PATENT DOCUMENTS 2,962,520 11/1960 Schrader .............................. 260/973
3,014,943 12/1961 Schegk et al. ....................... 260/973
4,190,652 2/1980 Hofer et al. ......................... 260/973

OTHER PUBLICATIONS

V. D. Akamsin and N. I. Rizpolozhenskii, "Esters of Trivalent Phosphorus Thioacids," Dec. 1, 1966 (submitted). Translated from Izvestiya Akademii Nauk SSSR, Seriya Khimicheskaya, No. 9, pp. 1983–1986, Sep., 1967.

Primary Examiner—Anton H. Sutto
Attorney, Agent, or Firm—Burns, Doane, Swecker & Mathis

[57] ABSTRACT

Compounds useful as intermediates for insecticides and nematocides having the formula

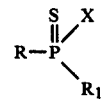

in which
R is alkyl of 1 to 6 carbon atoms;
$R_1$ is branched alkyl of 3 to 8 carbon atoms; and
X is halogen are disclosed as well as their preparation by direct reaction of an alkylphosphonothioic dihalide with a branched alkyl thiol.

8 Claims, No Drawings

PROCESS FOR THE PRODUCTION OF S-TERTIARYALKYL PHOSPHONODITHOIC HALIDES

This is a cross reference to related application continuation of copending application Ser. No. 071,465, filed Aug. 31, 1979, now abandoned.

The intermediates disclosed herein are converted to compounds useful as insecticides and nematocides as disclosed in an application entitled "UNSYMMETRICAL THIOPHOSPHONATE INSECTICIDES AND NEMATOCIDES" filed on the same date as this application in the name of Jerry G. Strong, which application is incorporated herein by reference.

SUMMARY OF THE INVENTION

This invention relates to compounds of the formula $$R-P\underset{R_1}{\overset{S}{\underset{\|}{\diagup}}}\overset{X}{\diagdown}$$

and the process of their preparation by reaction of $$R-P\underset{X}{\overset{S}{\underset{\|}{\diagup}}}\overset{X}{\diagdown}$$

with $R_1SH$ solvent, at a temperature of about 20° C. to 100° C. in the presence of a base; in which
 R is alkyl of 1 to 6 carbon atoms;
 $R_1$ is branched alkyl of 3 to 8 carbon atoms; and
 X is halogen.

The compounds of this invention are useful as intermediates for the production of valuable insecticides nematocides as described in more detail hereinafter.

DETAILED DESCRIPTION OF THE INVENTION

One aspect of this invention is a class of branched-S-alkyl phosphonodithioic halide intermediates useful for the production of insecticides and nematocides.

A second aspect of this invention is a simple process for the production of branched-S-alkyl phosphonodithioic halides by the direct addition of thiols to alkylphosphonothioic dihalides.

The synthesis of S-alkyl alkylphosphonothioic halides is usually accomplished by methods other than the direct addition of thiols to alkylphosphonothioic dihalides because direct reaction is normally accompanied by an undesirable side reaction in which both halo atoms in the phosphonothioic dihalide are substituted with the alkyl thiol. The side reaction is a particular problem where normal alkyl thiols are used. Thus, when the synthesis of normal S-alkyl alkylphosphonodithioic chlorides is desired, alternative routes are usually employed.

I have discovered that branched alkylthiols react smoothly with alkylphosphonothioic dichloride to give mono addition of one thiol in good yield, according to the following equation:

$$RP\underset{X}{\overset{S}{\underset{\|}{\diagup}}}\overset{X}{\diagdown} + HSR_1 + base \xrightarrow{solvent} RP\underset{SR_1}{\overset{S}{\underset{\|}{\diagup}}}\overset{X}{\diagdown} + base.HX + base.H$$

In the above formulae:
 R is alkyl of 1 to 6 carbon atoms, particularly methyl or ethyl;
 $R_1$ is branched-alkyl of 3 to 8 carbon atoms, particularly iso-propyl, tert.-butyl or iso-butyl; and
 X is halogen, particularly chlorine.

Suitable reaction solvents include water and organic solvents. With water the base is advantageously an inorganic base such as sodium hydroxide. With organic solvents the base is advantageously a tertiary amine such as trimethylamine, triethylamine, pyridine, dimethyl aniline or diethyl aniline.

Suitable organic solvents include benzene, toluene, cyclohexane, acetone and 2-butanone.

Generally, the reaction is conducted at a temperature of between about 20° C. to 100° C. The temperature is critical only during the addition of the base which is introduced at a temperature of below 50° C. for the best yields. It has been found advantageous to add the tertiary amine to the other reactants at a temperature of about 20° C. to 30° C. and then to heat the entire reaction mixture to a temperature of about 70° C. to 80° C. to complete the reaction.

The reaction is normally carried out with an approximately equal molar ratio of the phosphonothioic dichloride, thiol and the base. An excess of about 10 to 20% of the phosphonothioic dichloride can be used relative to the other reactants. However, the use of a slight excess of the thiol and the base relative to the phosphonothioic dichloride (5–10% excess) did not appreciably affect the yield.

The following examples illustrate the process of this invention and the production of several specific compounds of the invention.

EXAMPLE 1

$$CH_3-P\underset{S-C(CH_3)_3}{\overset{S}{\underset{\|}{\diagup}}}\overset{Cl}{\diagdown}$$

To a solution of methylphosphonothioic dichloride (128.5 g, 0.86 mole) in 500 ml toluene, was added 2-methyl-2-propanethiol (54 g, 0.6 mole) in one portion. Triethylamine (60 g, 0.6 mole) was added dropwise at room temperature (25°–30° C.) while stirring the reaction mixture. The mixture was let stand overnight, then heated to 70°–80° C. for three hours, then allowed to cool to room temperature. The reaction mixture was successively washed with water, cold 5% HCl solution, and water again, and dried over anhydrous $MgSO_4$. Then the solvent was stripped off to obtain a crude oily product which was distilled under vacuum. One hundred grams of the title product was obtained (82.3% yield), b.p. 72°–75° C./0.2 mm. $^1$H-NMR spectrum in chloroform-d ($Me_4Si$) confirmed the structure.

EXAMPLE 2

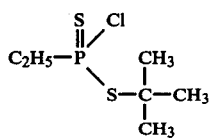

To a solution of ethylphosphonothioic dichloride, (16.3 g, 0.1 mole) in 50 ml toluene, was added in one portion 10 g of 2-methyl-2-propanethiol (0.11 mole). Triethylamine (12 g, 0.12 mole) was added dropwise while stirring the reaction mixture. Stirring was continued after the complete addition of the amine overnight at room temperature. The reaction mixture was heated up to 70° C. for one half hour, and let cool to room temperature. Then it was washed successively with water, cold 5% solution HCl, and again water and dried over anhydrous MgSO$_4$. The solvent was stripped off and the residual oil was subjected to high vacuum (0.05 mm) at room temperature for one hour. This product weighed 16.5 g (76% yield). The pure compound boils at 75°–78° C./0.7 mm. It has an $^1$H-NMR spectrum that conforms with the structure of the title compound.

EXAMPLE 3

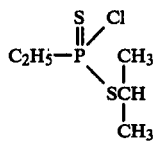

To a solution of ethylphosphonothioic dichloride (40 g, 0.25 mole) and 2-propanethiol (19 g, 0.027 mole) in 200 ml toluene, was added, dropwise, triethylamine (30 g, 0.3 mole) while stirring the reaction mixture, and maintaining the temperature of the reaction between 25°–30° C. After the complete addition of the amine, the reaction mixture was stirred at room temperature for two hours and let stand overnight. Workup as described for example 1 resulted in 25 g of product (50% yield) b.p. 85°–88° C./0.7 mm. The $^1$H-NMR spectrum of this product confirms the tile structure.

EXAMPLE 4

This example illustrates the utility of a compound of this invention as an intermediate in the synthesis of an insecticide and nematocide.

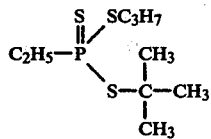

To a solution of S-tert.-butyl ethylphosphonodithioic chloride (15 g, 0.07 mole) in 50 ml 2-butanone, was added 1-propanethiol (6.6 g, 0.09 mole), and triethylamine (10 g, 0.1 mole). The mixture was refluxed under nitrogen for three hours, then let stand at room temperature overnight. The amine hydrochloride was filtered and the solvent was evaporated under vacuum. Ether (100 ml) was added and the solution was washed with water (50 ml), followed by 5% NaOH solution (50 ml), then water (twice 50 ml each). The ether solution was dried over anhydrous magnesium sulfate and the solvent was evaporated under vacuum. The residual oil was distilled to give the title compound, b.p. 102° C./0.4 mm. The product weighed 14.5 g (81% of theoretical yield). $^1$H-NMR spectrum confirmed the structure.

The above compound finds particular utility in the control of corn rootworm and exhibits low phytotoxicity to corn described in the copending application of Jerry G. Strong referred to above, which application is incorporated herein by reference.

I claim:

1. The process of preparing compounds of the formula

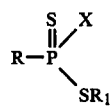

which comprises reacting

with R$_1$SH in a solvent in the presence of a base at a temperature of about 20° C. to 100° C.; in which
  R is alkyl of 1 to 6 carbon atoms;
  R$_1$ is tertiary alkyl of 4 to 8 carbon atoms; and
  X is halogen.

2. The process of claim 1 in which R$_1$ is tert.-butyl.

3. The process of claim 1 in which X is chloro.

4. The process of claim 1 in which said solvent is benzene, toluene, cyclohexane, acetone or 2-butanone.

5. The process of claim 1 in which said base is trimethylamine, triethylamine, pyridine, dimethyl aniline or diethylaniline.

6. The process of claim 1 in which the tertiary amine is added to the other reactants dropwise at a temperature of about 20° C. to 30° C. and the entire reaction mixture is then heated to a temperature of 70° C. to 80° C.

7. The process of claim 1 in which said solvent is an aqueous solution of an inorganic base.

8. The process of claim 1 in which said solvent is aqueous sodium hydroxide.

* * * * *